(12) United States Patent
Kim (10) Patent No.: US 8,696,338 B2
(45) Date of Patent: Apr. 15, 2014

(54) APPARATUS FOR MANUFACTURING VEGETABLE GELATIN CAPSULE

(75) Inventor: Ju-su Kim, Seoul (KR)

(73) Assignee: Chang Sung Softgel System Ltd., Pocheon-si (KR)

( * ) Notice: Subject to any disclaimer, the term of this patent is extended or adjusted under 35 U.S.C. 154(b) by 12 days.

(21) Appl. No.: 13/475,065

(22) Filed: May 18, 2012

(65) Prior Publication Data

US 2012/0294975 A1 Nov. 22, 2012

(30) Foreign Application Priority Data

May 18, 2011 (KR) .......................... 10-2011-0047038
May 8, 2012 (KR) .......................... 10-2012-0048463

(51) Int. Cl.
*B29C 45/78* (2006.01)

(52) U.S. Cl.
USPC ............... 425/5; 425/143; 425/144; 425/547; 425/552

(58) Field of Classification Search
CPC ........................... B29C 45/78; B29C 45/7312
USPC .............................. 425/5, 143, 144, 547, 552
See application file for complete search history.

(56) References Cited

U.S. PATENT DOCUMENTS

| | | | | |
|---|---|---|---|---|
| 4,028,024 A | * | 6/1977 | Moreland | ............... 425/133.1 |
| 5,735,105 A | * | 4/1998 | Stroud et al. | ................. 53/411 |
| 7,247,010 B2 | * | 7/2007 | Victorov et al. | .................. 425/5 |
| 2005/0073066 A1 | * | 4/2005 | Victorov et al. | ............. 264/40.1 |
| 2010/0219543 A1 | * | 9/2010 | Zazula et al. | ................. 264/4.4 |
| 2011/0006457 A1 | * | 1/2011 | De Bock et al. | .............. 264/306 |
| 2012/0052118 A1 | * | 3/2012 | Altamar et al. | ............... 424/451 |

* cited by examiner

*Primary Examiner* — Tim Heitbrink
(74) *Attorney, Agent, or Firm* — Jefferson IP Law, LLP (57) ABSTRACT

An apparatus for manufacturing a capsule by using vegetable gelatin is provided. Heating units are installed in a gelatin feeding line, which feeds gelatin in the form of a sheet, and a molding line to feed the gelatin in a predetermined temperature. The molded capsule is conveyed through a conveyer so that the molded capsule is stably dried and cured and a temperature of the conveyer is adjusted to control a temperature of the capsule. A length of the drying line is maximally increased within a narrow space, so that a film of the capsule made of the vegetable gelatin is gradually cured and dried without abrupt temperature variation, thereby preventing crack from occurring in the capsule, and preventing bonding parts of the capsule from being torn to improve the commercial value of the capsule.

5 Claims, 8 Drawing Sheets

APPARATUS FOR MANUFACTURING VEGETABLE GELATIN CAPSULE

PRIORITY

This application claims the benefit under 35 U.S.C. §119(a) of a Korean patent application filed on May 18, 2011 in the Korean Intellectual Property Office and assigned Ser. No. 10-2011-0047038, and of a Korean patent application filed on May 8, 2012 in the Korean Intellectual Property Office and assigned Ser. No. 10-2012-0048463, the entire disclosures of which are hereby incorporated by reference.

BACKGROUND OF THE INVENTION

1. Field of the Invention

The present invention relates to an apparatus for manufacturing a capsule of vegetable gelatin. More particularly, the present invention relates to an apparatus for manufacturing a capsule of vegetable gelatin, in which the molded capsule is gradually cured through the curing process without abrupt temperature variation and the drying process is performed after the curing process has been performed for a predetermined period of time, thereby preventing the capsule from being torn or broken caused by the abrupt temperature variation during the curing and drying processes and allowing the capsule to have the desired hardness.

2. Description of the Related Art

In general, gelatin is mainly used as a material to form a film of a capsule because the gelatin is readily dissolved in a human body and has the superior surface strength and the stable humidity adsorption/desorption property. In most cases, animal gelatin derived from the livestock is used.

However, since the animal gelatin mainly consists of animal protein, the capsule may not contain materials that react with the protein and may cause the allergy to the person who takes in the animal gelatin. In particular, the animal gelatin is not suitable for vegetarians. Further, the use of the animal gelatin is more reluctant due to the bovine spongiform encephalopathy and foot-and-mouth diseases, which are infected to humans from the livestock.

In this regard, recently, a vegetable capsule, which is prepared by mixing glycerin and purified water with vegetable materials, such as modified starch and carrageenan, has been suggested as a substitute for the animal capsule. However, as compared with the animal gelatin, the property of vegetable gelatin is easily changed, so the vegetable gelatin may not be easily prepared and the defect rate may increase in the process for preparing the vegetable gelatin. In addition, crack may be generated in the vegetable capsule after the vegetable capsule has been manufactured, so the stability and commercial value of the vegetable capsule may be degraded.

That is, if the apparatus for manufacturing the animal gelatin capsule is used for manufacturing the vegetable gelatin capsule, the vegetable gelatin capsule cannot be obtained due to the difference in the physical property between the animal gelatin capsule and the vegetable gelatin capsule. In detail, when feeding the animal gelatin, the animal gelatin is heated, so liquid-phase animal gelatin is fed while flowing due to the deadweight thereof. However, since the vegetable gelatin has the high viscosity, the vegetable gelatin may not flow by the deadweight thereof, so the vegetable gelatin may not be fed in the form of a sheet having a uniform thickness. In addition, the animal gelatin can be stably dried even in the very-low temperature, but the physical property of the vegetable gelatin may be changed if the temperature is abruptly changed. Thus, the vegetable gelatin may not maintain the capsule shape. That is, the external appearance of the capsule may be deformed or the crack is generated in the capsule, so that the capsule is torn or broken.

SUMMARY OF THE INVENTION

Aspects of the present invention are to address at least the above-mentioned problems and/or disadvantages and to provide at least the advantages described below. Accordingly, an aspect of the present invention is to provide an apparatus for manufacturing a capsule by using vegetable gelatin, in which a source material melted in a liquid phase and including modified starch and carrageenan is automatically fed, cooling and drying temperatures are optimized in a line for feeding the liquid-phase gelatin in the form of a sheet and a line for forming the capsule, and a drying line is maximally lengthened in such a manner that the molded capsule can be gradually cured, so that the capsule can be stably dried, crack can be prevented from occurring in the capsule, and bonding parts of the capsule can be prevented from being torn, thereby improving the commercial value of the capsule.

In accordance with an aspect of the present invention, an apparatus for manufacturing a capsule is provided. In the apparatus, liquid-phase gelatin prepared by mixing vegetable materials including modified starch and carrageenan can be kept in the predetermined temperature by using a service tank equipped therein with a heating unit, a metering station is connected to the service tank to automatically feed the liquid-phase gelatin to a capsule forming device by using a pump, a heating unit is accommodated in a feeding drum that feeds gelatin sheets so that the gelatin sheet having the high temperature can be transferred to a molding frame to keep the viscosity of gelatin, a dry conveyer is installed between the capsule forming device and a tumble dryer to additionally perform the curing process for the capsule, and the capsule molded in the capsule forming device is fed to the tumble dryer after being subject to the curing process by way of the dry conveyer so that the surface of the capsule can be dried after the capsule has been cured.

In addition, the dry conveyer has the multi-layer structure to lengthen the convey route of the dry conveyer and the temperature of each layer of the dry conveyer is variously set, so the capsule can be gradually cured corresponding to the temperature of each layer.

Further, in the capsule forming device, a blowing tube is formed at the molding frame where the capsule is molded, and cold wind generated from an air conditioner is injected through the blowing tube so that the gelatin is prevented from adhering to the surface of the molding frame by the cold wind when the capsule is formed in the molding frame.

As described above, according to the present invention, when the vegetable gelatin is prepared and fed, the manufacturing line can be constantly kept in the predetermined temperature without the abrupt temperature variation, so the vegetable gelatin can be stably fed in the form of the sheet having the uniform thickness, so the capsule can be readily manufactured by using the existing apparatus for manufacturing the capsule. In addition, the capsule may have the desired shape and hardness, so the defect rate can be minimized and the stability can be improved, thereby improving the commercial value of the capsule.

Further, since the film of the capsule is formed by using the vegetable gelatin, the side-effect and the limitations in use of the capsule can be minimized and the unpleasant feeling of the person who takes in the capsule can be reduced.

Other aspects, advantages, and salient features of the invention will become apparent to those skilled in the art from the following detailed description, which, taken in conjunction with the annexed drawings, discloses exemplary embodiments of the invention.

BRIEF DESCRIPTION OF THE DRAWINGS

The above and other aspects, features, and advantages of certain exemplary embodiments of the present invention will be more apparent from the following description taken in conjunction with the accompanying drawings, in which.

Throughout the drawings, it should be noted that like reference numbers are used to depict the same or similar elements, features, and structures.

DETAILED DESCRIPTION OF EXEMPLARY EMBODIMENTS

The following description with reference to the accompanying drawings is provided to assist in a comprehensive understanding of exemplary embodiments of the invention as defined by the claims and their equivalents. It includes various specific details to assist in that understanding but these are to be regarded as merely exemplary. Accordingly, those of ordinary skill in the art will recognize that various changes and modifications of the embodiments described herein can be made without departing from the scope and spirit of the invention. In addition, descriptions of well-known functions and constructions may be omitted for clarity and conciseness.

The terms and words used in the following description and claims are not limited to the bibliographical meanings, but, are merely used by the inventor to enable a clear and consistent understanding of the invention. Accordingly, it should be apparent to those skilled in the art that the following description of exemplary embodiments of the present invention is provided for illustration purpose only and not for the purpose of limiting the invention as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

A capsule forming device 200 forms a film of a capsule by using gelatin. In general, the gelatin contained in a service tank 100 is fed to the capsule forming device 200 through a convey line and coated on feeding drums 210, which are provided at both sides of the capsule forming device 200 in correspondence with each other, in the form of a sheet. Then, the gelatin in the form of the sheet is fed into a central portion of the capsule forming device 200 to mold the gelatin in the form of a capsule, thereby providing the gelatin capsule. The gelatin capsule is fed to a tumble dryer 400 where the film of the gelatin capsule is dried.

According to an exemplary embodiment of the present invention, the capsule is formed by using vegetable gelatin other than animal gelatin, which is formed and dried in the low temperature, while allowing the capsule to have the desired shape and proper hardness. The vegetable gelatin is fed in the form of a sheet and molded in the high temperature and the capsule, which has been molded in the capsule forming device 200, is fed to a dry conveyer 300 before the capsule is dried in the tumble dryer 400, so that the cooling process, that is, the curing process for the capsule is gradually and stably performed while the capsule is moving along the dry conveyer 300.

Figure 1:
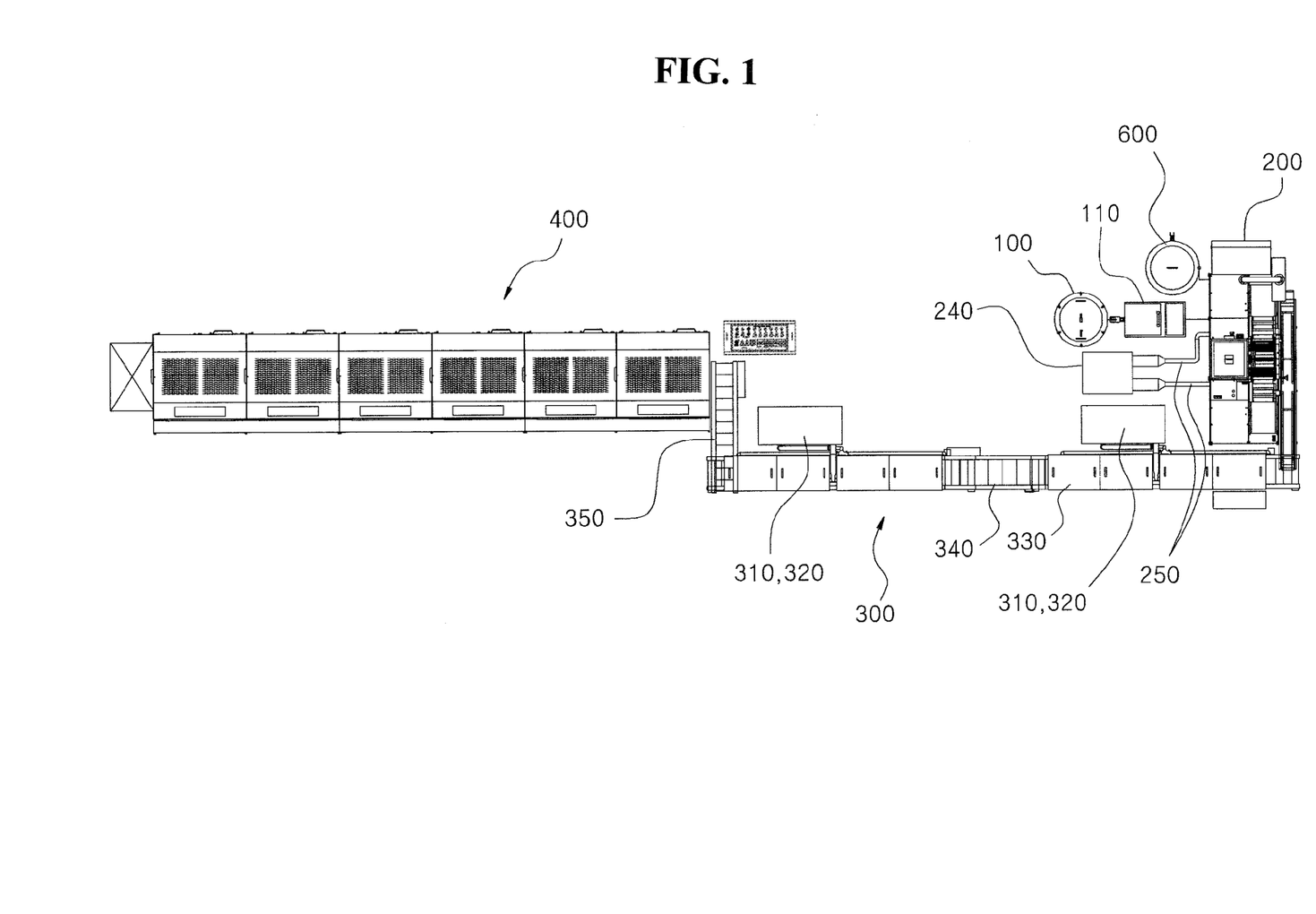
FIG. 1 is a plan view showing a structure of an apparatus according to an exemplary embodiment of the present invention.
Figure 2:
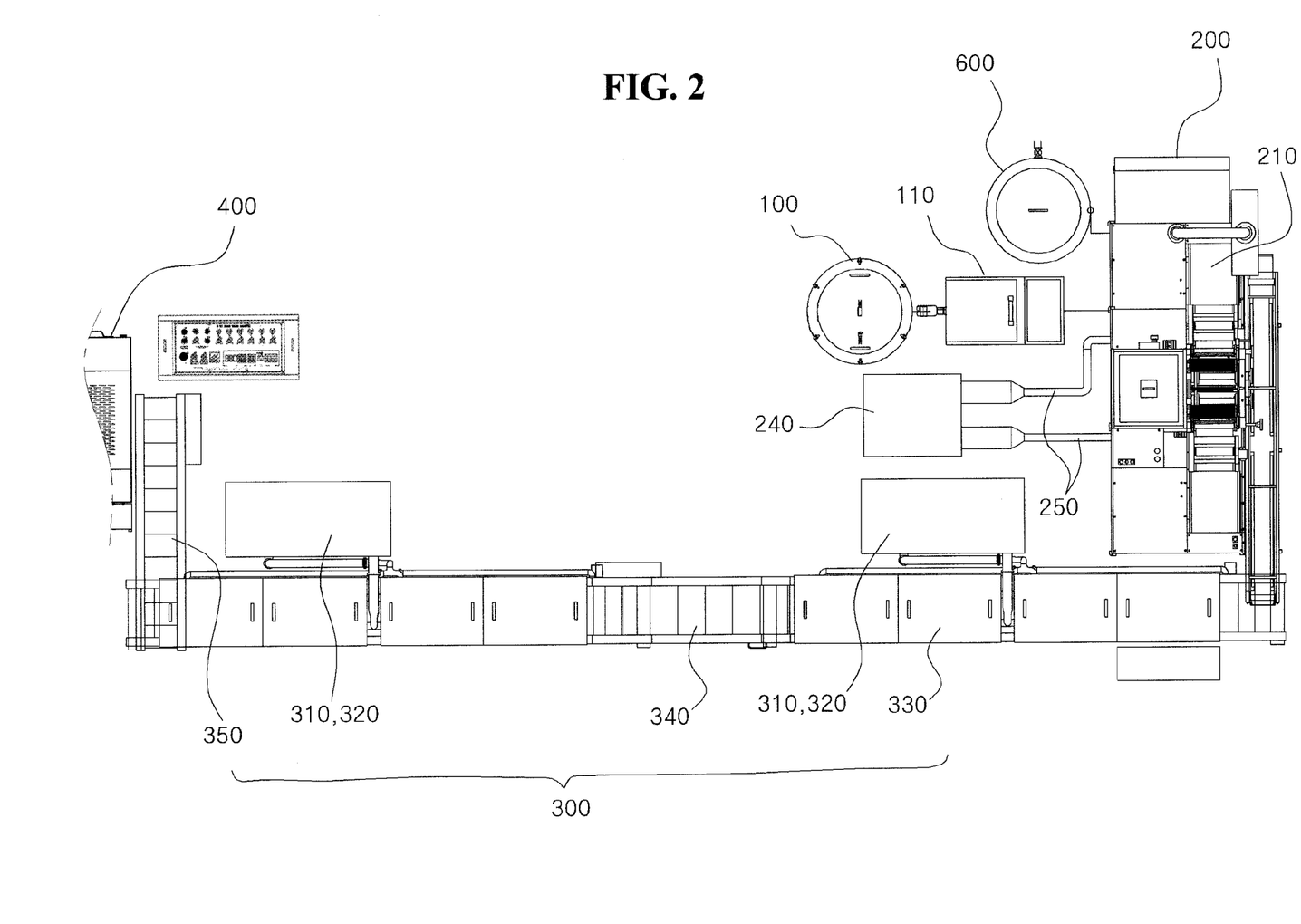
FIG. 2 is a partially enlarged view showing the detailed structure of a conveyer illustrated in FIG. 1 according to an exemplary embodiment of the present invention.
Figure 3:
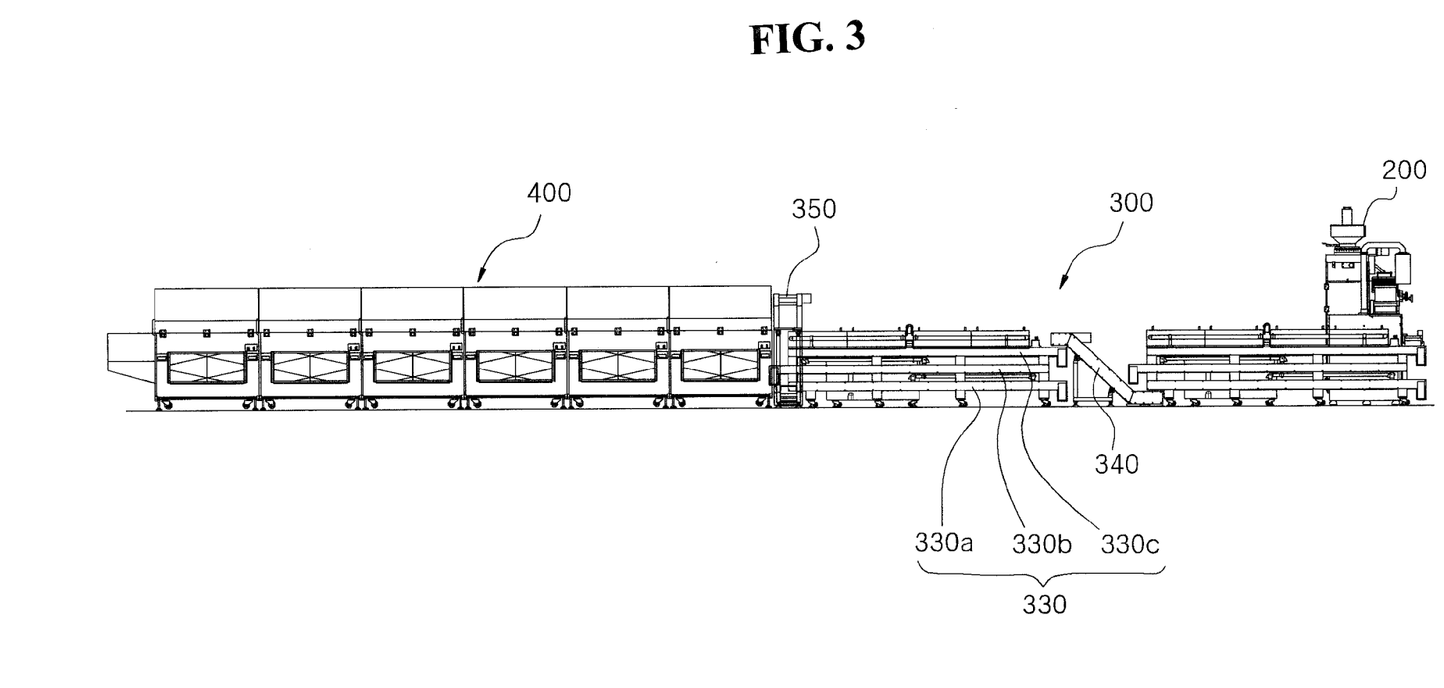
FIG. 3 is a side view showing a structure of an apparatus according to an exemplary embodiment of the present invention.
Figure 4:
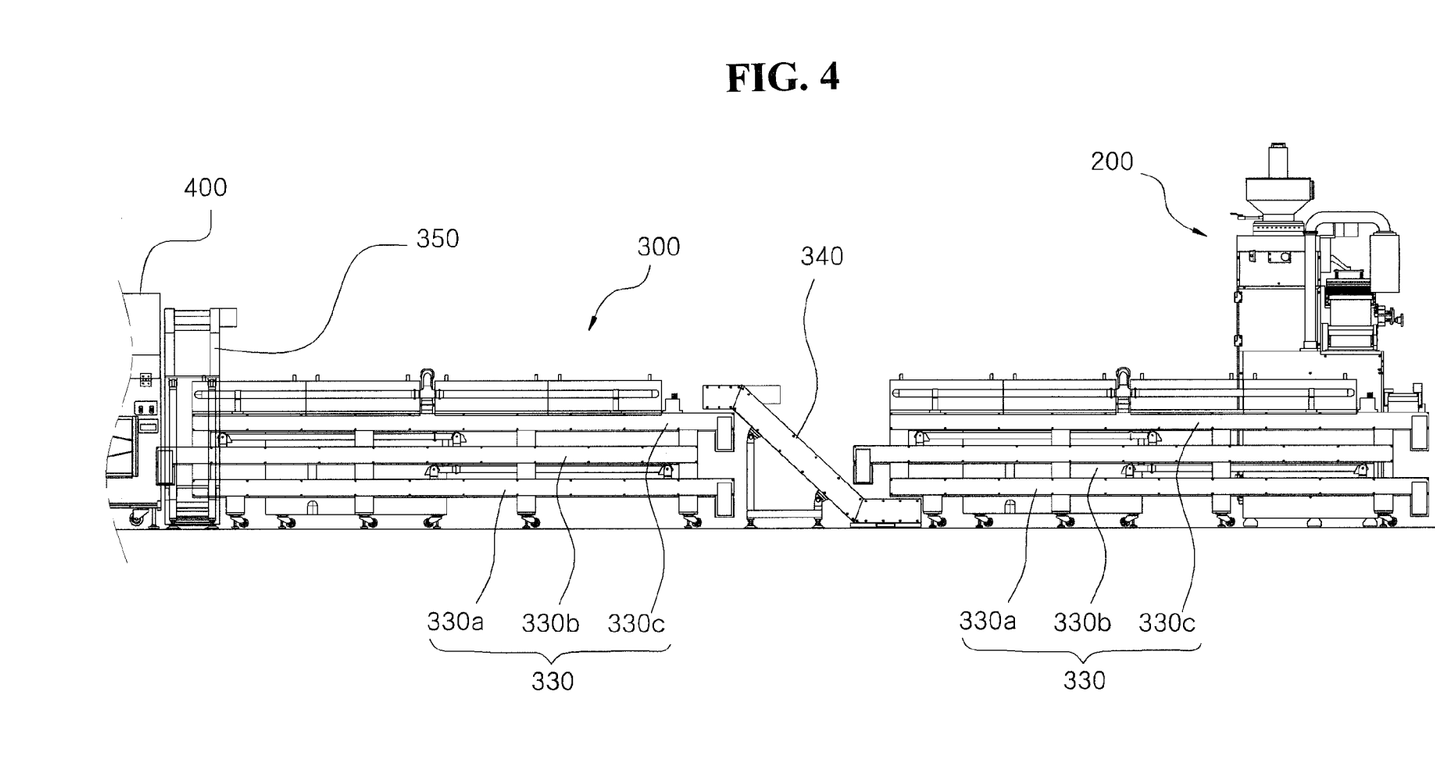
FIG. 4 is a partially enlarged view showing the detailed structure of a conveyer illustrated in FIG. 3 according to an exemplary embodiment of the present invention.

Referring to FIGS. 1 and 2, the dry conveyer 300 is installed between the capsule forming device 200 and the tumble dryer 400 to convey and cure the capsule. In addition, the temperature of a conveyer belt 330, which conveys the capsule in the dry conveyer 300, can be adjusted by a heating blower 310 and a cooling blower 320, so that the temperature of the capsule can be set while the capsule is being conveyed.

That is, if the capsule is formed by using the vegetable gelatin, the capsule may be torn or broken when the liquid-phase gelatin heated with the high temperature is rapidly cooled, so the capsule must be gradually cooled and cured under the constant temperature condition in all processes. As described above, since the dry conveyer 300 is installed between the capsule forming device 200 and the tumble dryer 400, the cooling process for the capsule can be carried out while the capsule is being conveyed. In addition, the temperature of the capsule can be stably lowered without the abrupt temperature variation by adjusting the temperature of the conveyer belt 330.

At this time, if the conveyer belt 330 is configured to have the two-layer structure, the three-layer structure or the multi-layer structure, the dry conveyer 300 may lengthen the convey route of the capsule, which has been molded, so that the capsule can be more gradually cooled and cured. In addition, the temperature of each conveyer layer 330a, 330b, . . . or 330n is variously set in such a manner that the cooling temperature of the capsule can be gradually lowered.

That is, when the capsule is manufactured by using the vegetable gelatin, the feeding drums 210 are maintained at the temperature of about 45° C. Thus, if the conveyer belt 330 has the three-layer structure, the third layer is maintained at the temperature of about 30° C. to 40° C., and the first and second layers are maintained at the temperature of about 20° C. to 25° C. in such a manner that the capsule can be gradually cooled and cured while the capsule is being conveyed through the dry conveyer 300.

At this time, if at least two conveyer belts 330 having the multi-layer structure are repeatedly provided in the dry conveyer 300, the convey route for the capsule can be more lengthened and the capsule can be more gradually cooled and cured by reducing the temperature difference among the conveyer layers.

In addition, if a plurality of dry conveyers 300 are provided, a middle conveyer 340 is provided at a connection part of the dry conveyers 300 to connect the convey route for the capsule. In addition, an end conveyer 350 is installed between the dry conveyer 300 and the tumble dryer 400 to feed the capsule from the dry conveyer 300 to the tumble dryer 400.

Further, if the dry conveyer 300 is configured to have the multi-layer structure, the middle conveyer 340 and the end conveyer 350 are provided between the lower layer and the upper layer of the dry conveyer 300 to connect the conveyer belts 330 with each other or to connect the conveyer belts 330 with the tumble dryer 400 such that the capsule can be readily conveyed through the free fall.

Meanwhile, the tumble dryer 400 where the drying process is performed for the capsule that has passed through the dry conveyer 300 may have the multi-stage structure such that the capsule may be dried while passing through each stage. Wind is injected into each stage of the tumble dryer 400 as an inner tub is rotated. At this time, since the vegetable gelatin has the low stability, the drying structure of each stage of the tumble dryer 400 is variously set to stably dry the molded capsule.

In other words, at each stage of the tumble dryer 400, the capsule can be dried through the rotation of the inner tub or by blowing wind while the inner tub is rotating. Preferably, at the stages provided in the front portion of the tumble dryer 400 where the capsule has the low stability, the capsule is dried only through the rotation of the inner tub. In addition, at the stages provided in the rear portion of the tumble dryer 400, the capsule is dried by blowing wind while the inner tub is rotating.

For instance, if the tumble dryer 400 has the six-stage structure, the wind is not injected into the first and second stages and the wind is injected into the third to sixth stages because the stability of the capsule can be improved in the rear portion of the tumble dryer 400, thereby improving the drying efficiency for the capsule.

Figure 5:
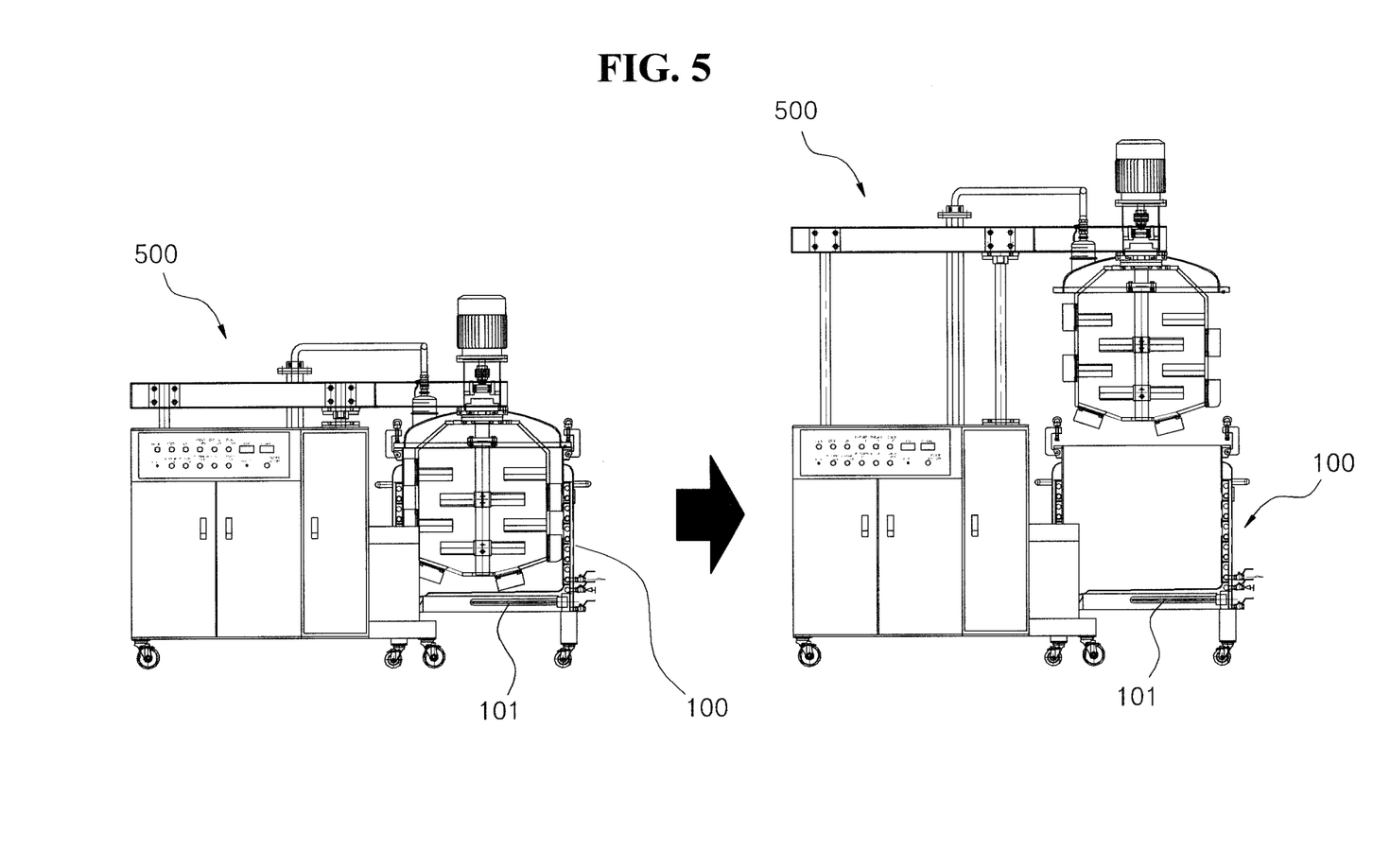
FIG. 5 is a schematic view showing a structure of a stirrer and a tilting structure of a service tank used for manufacturing vegetable gelatin according to an exemplary embodiment of the present invention.

Meanwhile, the vegetable gelatin is prepared by mixing glycerin and purified water with modified starch and carrageenan in a predetermined composition ratio. At this time, the vegetable materials are mixed and melted by a stirrer 500 to prepare the liquid-phase gelatin.

If the service tank 100 has the tilting structure, it is not necessary to transfer the liquid-phase gelatin to other storage vessels, so the service tank 100 is moved and connected to the capsule forming line when the liquid-phase gelatin has been prepared. In addition, if a heating device 101 is installed in the service tank 100, the gelatin can be melted by heating the service tank 100 during the melting process for the gelatin. Further, the temperature of the gelatin can be constantly maintained while the service tank 100 is being moved and the gelatin is being fed from the service tank 100 connected to the capsule forming line, so that gelatin can be maintained in the liquid phase without being solidified.

At this time, an upper end of the service tank 100 is covered with a lid 102 to seal an interior of the service tank 100. In addition, an inlet 103 is formed in the lid 102 to inject air through the inlet 103. As the air is injected through the inlet 103, the internal pressure of the service tank 100 is increased so that the liquid-phase gelatin can be transferred to a metering station 110.

Figure 6:
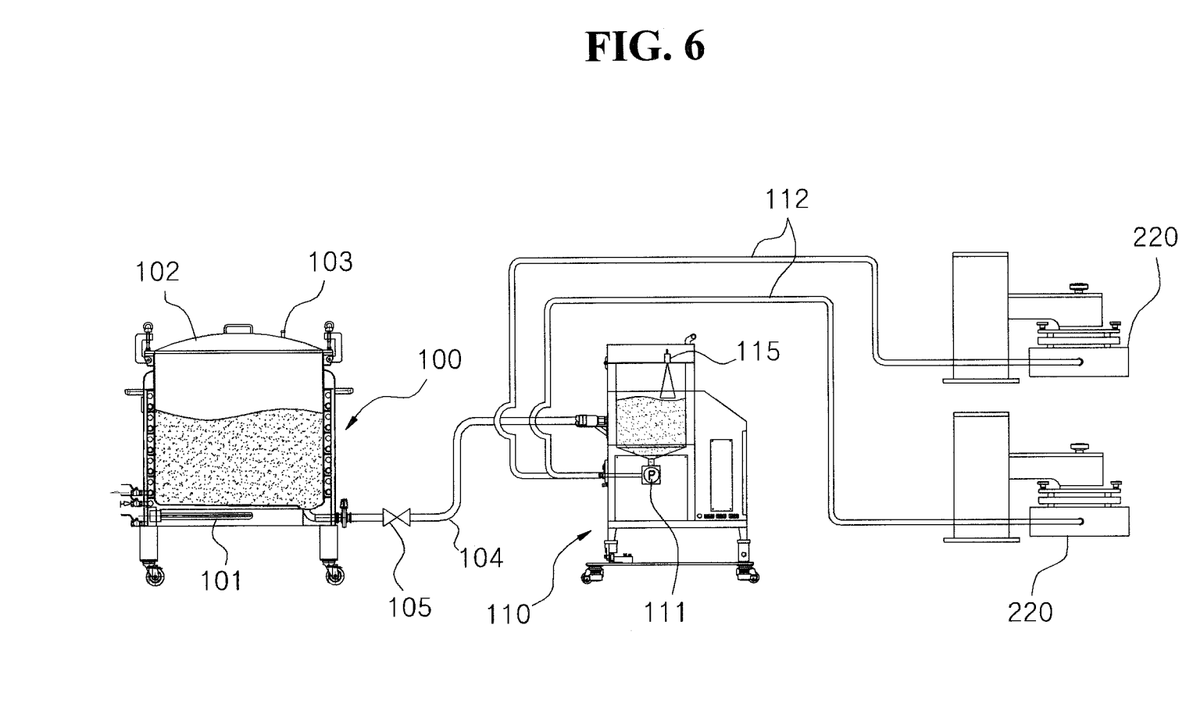
FIG. 6 is a schematic side view showing a feeding route of liquid-phase gelatin according to an exemplary embodiment of the present invention.
Figure 7:
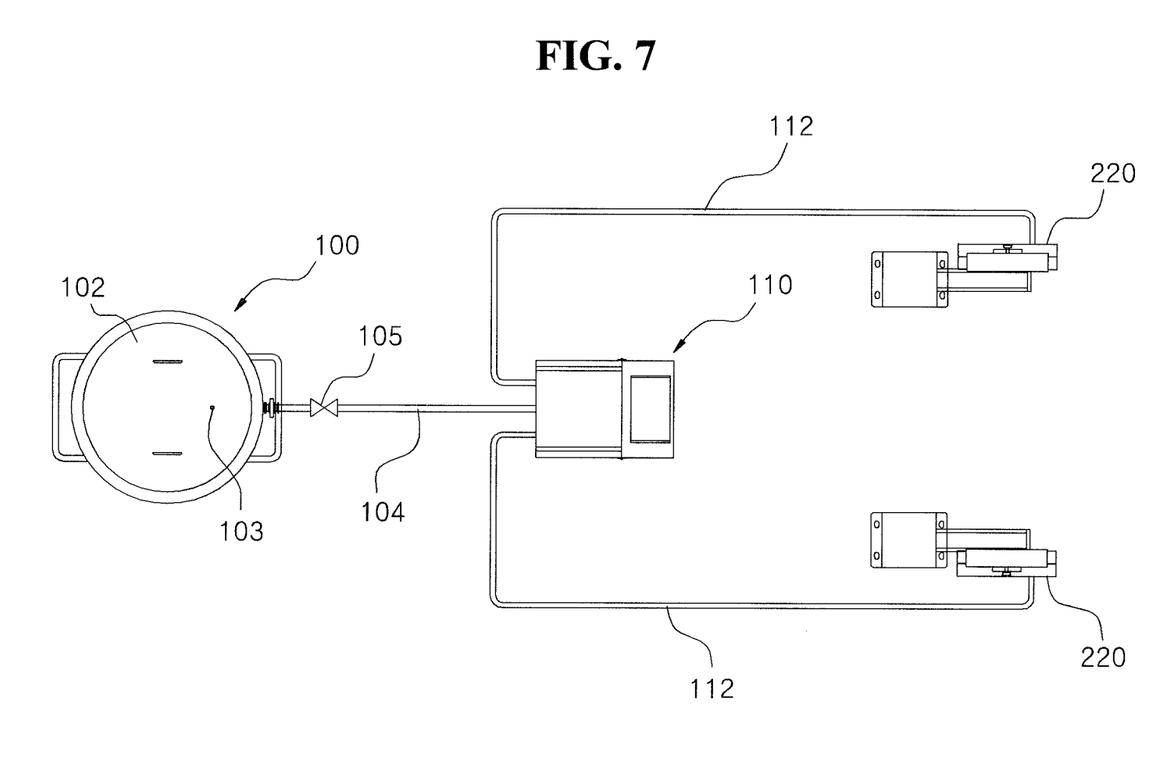
FIG. 7 is a schematic plan view showing a feeding route of liquid-phase gelatin according to an exemplary embodiment of the present invention.

In order to allow the liquid-phase vegetable gelatin, which is transferred to the metering station 110, to be coated on the feeding drums 210 in the form of a sheet, it is necessary to push the liquid-phase vegetable gelatin through a slot die 220. To this end, a pump 111 is installed in the metering station 110 and a feeding line 112, which is connected to the slot diode 220, is connected to the pump 111. Thus, the liquid-phase vegetable gelatin, which is forcibly transferred from the metering station 110, is forcibly discharged in the form of the sheet through the slot die 220, so that the sheet-shape gelatin can be coated on the feeding drums 210 with a uniform thickness.

In addition, an opening/closing valve 105 is installed in a hose 104 connecting the service tank 100 with the metering station 110 to convey the gelatin. Further, a sensor 115 is accommodated in the metering station 110 to detect the storage capacity of the gelatin. The opening/closing valve 105 is operated by the sensor 115. In detail, the opening/closing valve 105 is automatically open or closed according to the storage capacity of the gelatin in the metering station 110 to continuously feed the gelatin.

Therefore, the gelatin can be maintained in the predetermined temperature while the liquid-phase gelatin serving as the source material for the capsule is being fed or discharged. In addition, although the vegetable gelatin is used to form the film of the capsule, since the vegetable gelatin is discharged in the form of the sheet and coated with the uniform pressure and thickness, the film of the capsule made of the vegetable gelatin can be prepared in a state that the vegetable gelatin is coated on the surface of the feeding drums in a thin thickness.

In addition, the gelatin fed to the capsule forming device 200 is heated in the service tank 100 and then fed from the service tank 100 under the high temperature condition. In detail, a heating unit (not shown) is accommodated in the feeding drums 210 so that the gelatin sheet can be subject to the manufacturing process under the high temperature condition.

That is, when the gelatin is in a sheet state, the feeding drums 210 maintain the high temperature condition by using the heating unit. In addition, when the capsule has been formed in the capsule forming device, the temperature is gradually lowered to dry the capsule such that the capsule can be slowly cured, thereby preventing the bonding part from being torn and minimizing the defect rate. Thus, the capsule can be stably manufactured.

Figure 8:
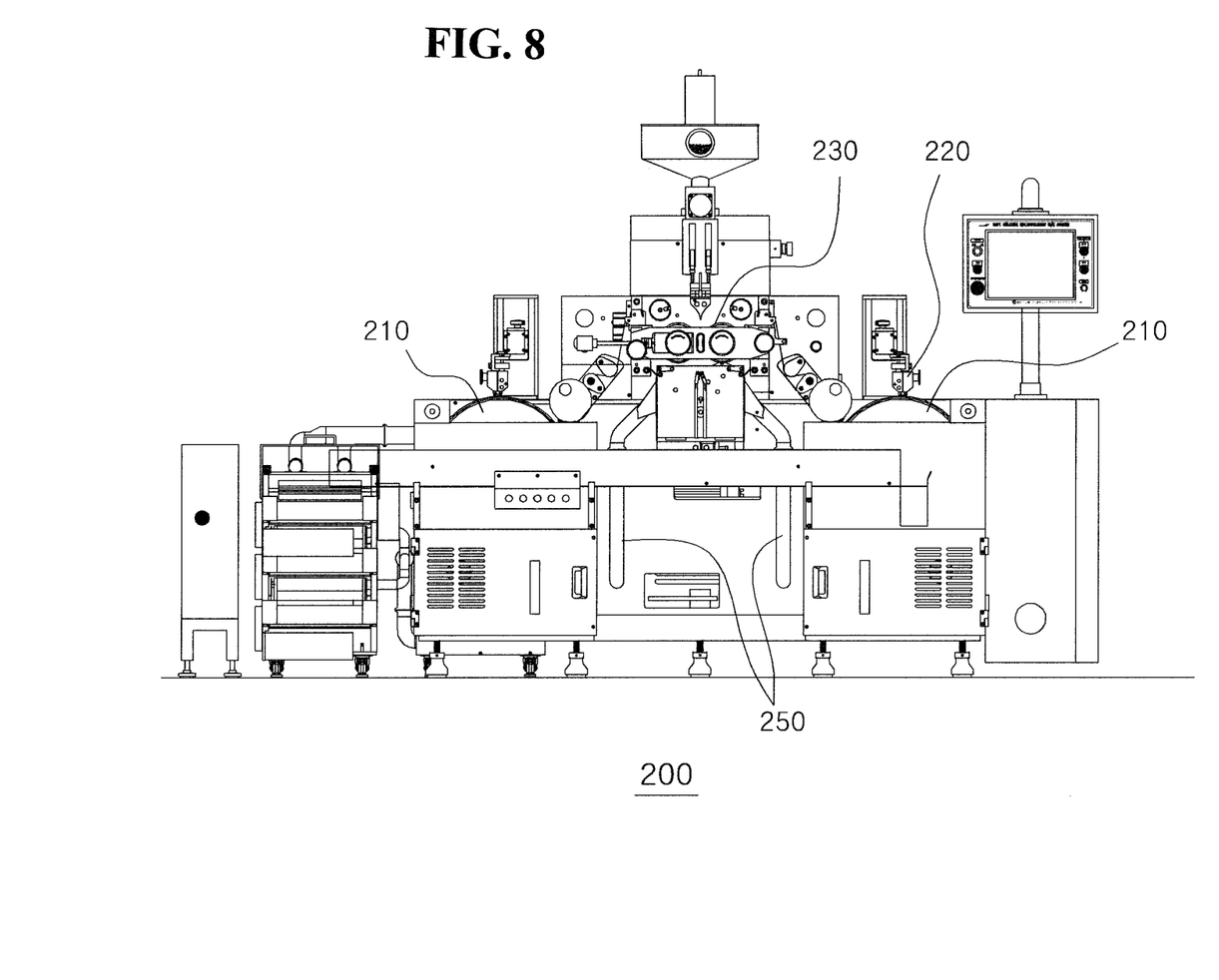
FIG. 8 is a front view showing a structure of a capsule forming device according to an exemplary embodiment of the present invention.

In addition, when the capsule is manufactured by using the gelatin having the high temperature, the surface of the capsule may adhere to an inner surface of a molding frame 230. In this regard, cold wind is blown to the molding frame 230 to instantly cure the surface of the capsule, so that the gelatin is prevented from adhering to the surface of the molding frame 230. In order to blow the cold wind, an air conditioner 240 is independently provided and the molding frame 230 is connected to the air conditioner 240 through a feeding tube 250 such that the cold wind generated from the air conditioner 240 can be blown to the molding frame 230 through the feeding tube 250, thereby preventing the surface of the capsule from adhering to the molding frame 230 when the capsule is formed. In addition, tension can be applied by strengthening a net. That is, residues, which may remain after the capsule has been formed, may be cured and compressed, so the residues can be readily separated from the capsule.

While the invention has been shown and described with reference to certain exemplary embodiments thereof, it will be understood by those skilled in the art that various changes in form and details may be made therein without departing from the spirit and scope of the invention as defined by the appended claims and their equivalents.

What is claimed is:

1. An apparatus for manufacturing vegetable gelatin capsule, the apparatus comprising:
   a service tank into which liquid-phase vegetable gelatin is fed;
   a metering station connected to the service tank;
   a capsule forming device into which the liquid-phase vegetable gelatin is fed through the metering station; and a dry conveyer and a tumble dryer, the dry conveyer positioned between the capsule forming device and the tumble dryer to convey and cure the vegetable gelatin capsule, wherein the dry conveyer is equipped with a heating blower and a cooling blower to control a temperature of a conveyer belt that conveys the vegetable gelatin capsule in order to adjust a curing temperature of the vegetable gelatin capsule in a predetermined temperature in such a manner that the vegetable gelatin capsule is stably cured without abrupt temperature variation.

2. The apparatus of claim 1, wherein compression air is injected into the service tank in a pneumatic manner to convey the liquid-phase vegetable gelatin contained in the service tank to the metering station, the metering station is equipped with a pump to automatically inject the gelatin into a slot die of the capsule forming device, and the liquid-phase vegetable gelatin is forcibly discharged in a form of a sheet through the slot die.

3. The apparatus of claim 2, wherein the service tank is provided therein with a heating device to maintain a temperature of the gelatin, the service tank is connected to the metering station through a hose for conveying the gelatin, an opening/closing value is installed in the metering station, and a sensor is provided in the metering station to detect a storage capacity of the gelatin in the metering station such that the gelatin is automatically fed based on the storage capacity of the gelatin in the metering station.

4. The apparatus of claim 1, wherein the capsule forming device includes feeding drums provided therein with heating units so that the gelatin having a high temperature is fed into the capsule forming device, a feeding tube that feeds cold air generated from an air conditioner is connected to a molding frame where the capsule is molded, the cold air generated from the air conditioner is blown to the molding frame through the feeding tube to prevent a surface of the capsule from adhering to the molding frame when the capsule is molded.

5. The apparatus of claim 1, wherein the dry conveyer includes a conveyer belt having a multi-layer structure to lengthen a convey route of the capsule that has been molded, and a temperature of each layer of the conveyer belt is gradually lowered to slowly cure the capsule.

* * * * *